(12) United States Patent
Williams et al.

(10) Patent No.: US 11,071,541 B2
(45) Date of Patent: Jul. 27, 2021

(54) LOADING UNIT INCLUDING SHIPPING MEMBER

(71) Applicant: Covidien LP, Mansfield, MA (US)

(72) Inventors: Justin Williams, Southbury, CT (US); Christopher Penna, Guilford, CT (US); Paul A. Scirica, Huntington, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/027,609

(22) Filed: Jul. 5, 2018

(65) Prior Publication Data
US 2018/0310934 A1    Nov. 1, 2018

Related U.S. Application Data

(62) Division of application No. 14/308,731, filed on Jun. 19, 2014, now Pat. No. 10,039,546.

(60) Provisional application No. 61/919,861, filed on Dec. 23, 2013.

(51) Int. Cl.
*A61B 17/072* (2006.01)
*A61B 17/115* (2006.01)
*A61B 17/00* (2006.01)
*A61B 90/00* (2016.01)

(52) U.S. Cl.
CPC ........ *A61B 17/072* (2013.01); *A61B 17/1155* (2013.01); *A61B 2017/0023* (2013.01); *A61B 2017/00473* (2013.01); *A61B 2017/07214* (2013.01); *A61B 2017/07271* (2013.01); *A61B 2090/038* (2016.02)

(58) Field of Classification Search
CPC .............................................. A61B 2017/0688
See application file for complete search history.

(56) References Cited

U.S. PATENT DOCUMENTS

| 4,505,272 A | 3/1985 | Utyamyshev et al. |
| 4,881,544 A | 11/1989 | Green et al. |
| 4,930,674 A * | 6/1990 | Barak .................. A61B 17/072 227/179.1 |
| 5,669,918 A | 9/1997 | Balazs et al. |
| 5,836,503 A | 11/1998 | Ehrenfels et al. |
| 7,182,239 B1 | 2/2007 | Myers |

(Continued)

FOREIGN PATENT DOCUMENTS

| CN | 102579096 A | 7/2012 |
| EP | 2462875 A2 | 6/2012 |

(Continued)

OTHER PUBLICATIONS

European Search Report 14199687.6-1654 dated May 12, 2015.
Chinese Office Action dated Apr. 4, 2018 in Chinese Appln. No. 201410806443.

*Primary Examiner* — Hemant Desai
*Assistant Examiner* — Tanzim Imam
(74) *Attorney, Agent, or Firm* — Carter, DeLuca & Farrell LLP

(57) ABSTRACT

A loading unit including a shipping member is provided. The loading unit includes a housing, a staple pushing assembly, a knife assembly, and a staple cartridge. The shipping member is configured to be selectively secured to the housing of the loading unit and prevents advancement of the staple pushing assembly and the knife assembly. The shipping member also retains staples within the staple cartridge.

20 Claims, 6 Drawing Sheets

(56) References Cited

U.S. PATENT DOCUMENTS

| | | |
|---|---|---|
| 8,006,701 B2 | 8/2011 | Bilotti et al. |
| 8,118,206 B2 | 2/2012 | Zand et al. |
| 8,328,060 B2 | 12/2012 | Jankowski et al. |
| 10,039,546 B2 | 8/2018 | Williams et al. |
| 2003/0178465 A1 | 9/2003 | Bilotti et al. |
| 2005/0139635 A1 | 6/2005 | Wukusick et al. |
| 2005/0222616 A1* | 10/2005 | Rethy .................. A61B 17/105 606/215 |
| 2009/0082777 A1 | 3/2009 | Milliman et al. |
| 2010/0147921 A1* | 6/2010 | Olson .................. A61B 17/068 227/175.1 |
| 2010/0163598 A1 | 7/2010 | Belzer |
| 2012/0085808 A1 | 4/2012 | Ehrenfels |
| 2012/0145767 A1 | 6/2012 | Shah et al. |
| 2012/0168486 A1* | 7/2012 | Ingmanson .......... A61B 17/072 227/176.1 |
| 2012/0234894 A1 | 9/2012 | Kostrzewski |
| 2013/0146643 A1 | 6/2013 | Schmid et al. |
| 2013/0214024 A1* | 8/2013 | Takei .................. A61B 17/068 227/175.1 |

FOREIGN PATENT DOCUMENTS

| | | |
|---|---|---|
| EP | 2499987 A2 | 9/2012 |
| EP | 2604195 A1 | 6/2013 |
| EP | 2604197 A2 | 6/2013 |
| EP | 2638866 A2 | 9/2013 |
| WO | 03079909 A2 | 10/2003 |
| WO | 2013026402 A1 | 2/2013 |

* cited by examiner

LOADING UNIT INCLUDING SHIPPING MEMBER

CROSS-REFERENCE TO RELATED APPLICATIONS

This application is a divisional of U.S. application Ser. No. 14/308,731, filed Jun. 19, 2014, which claims the benefit of and priority to U.S. Provisional Patent Application No. 61/919,861, filed Dec. 23, 2013. The entire content of each of the above applications is incorporated by reference herein.

BACKGROUND

Technical Field

The present disclosure relates to surgical stapling devices including replaceable loading units. More particularly, the present disclosure relates to replaceable loading units including a shipping member.

Background of Related Art

Surgical devices for applying staples, clips, or other fasteners to tissue are well known. Endoscopic surgical devices for applying surgical fasteners include an actuation unit, i.e., a handle assembly for actuating the device and a shaft for endoscopic access, and a tool assembly disposed at a distal end of the shaft. Certain of these devices are designed for use with a replaceable loading unit which includes the tool assembly and houses the staples or fasteners. The replaceable loading unit may include staples of various sizes and the staples may be arranged in one or more configurations. After firing the stapler with a replaceable loading unit, the user may remove the empty loading unit, select and attach to the stapler another loading unit having staples of the same or different size and the same or different staple arrangement, and fire the stapler again. This process may be performed repeatedly during a surgical procedure.

Many loading units typically include a staple cartridge, a staple pusher assembly, and, optionally, a knife assembly. Loading units including a knife assembly have the benefit of providing a new knife with each loading unit. The staple pusher assembly and the knife assembly generally include one or more movable parts positioned to engage one or more drive members of the actuation unit. If the moving parts are not properly retained in a proper position prior to and during attachment of the loading unit to the actuation unit, the loading unit may not properly engage the actuation unit, and thus, may not function properly. Some loading units are provided with automatic locking systems which block movement of the components of the loading unit prior to attachment of the loading unit to the actuation unit and allow free movement of the movable parts of the loading unit once the loading unit has been properly positioned on the actuation unit. However, these automatic locking systems are not configured to retain staples within the staple cartridge prior to activation of the loading unit.

Therefore, it would be beneficial to have a shipping member configured to maintain the movable parts of the loading unit and to maintain the staples within the staple cartridge.

SUMMARY

Accordingly, a loading unit including a shipping member is provided. The loading unit includes a housing, a staple pusher assembly operably retained within the housing, a knife assembly operably retained within the housing, and a staple cartridge disposed on a distal end of the housing and including a plurality of staples. The shipping member is selectively secured to the housing. A base portion includes an inner surface disposed adjacent the staple cartridge for maintaining the plurality of staples within the staple cartridge. A leg portion extends proximally from the base portion. A locking portion of the shipping member is disposed near a free end of the leg portion and is configured to selectively engage the housing and the knife assembly.

In some embodiments, the locking portion of the shipping member includes a latch member and the knife assembly includes a knife carrier having a lock member configured for selective engagement with the latch member of the locking portion. The knife carrier may be movable from an initial position in which the lock member of the knife carrier is engaged with the latch member of the shipping member to a retracted position in which the lock member is disengaged from the latch member. The shipping member may be secured to the housing when the knife carrier is in the initial position, and the lock member of the knife carrier may be engaged with the latch member of the locking portion of the shipping member. The shipping member may be separable from the housing when the knife carrier is in the retracted position. The knife carrier may be movable to an advanced position. The latch member may define an opening configured to selectively receive an engagement portion of the lock member when the knife carrier is in a distal position. The engagement portion of the lock member may extend parallel to a longitudinal axis of the housing. The locking portion of the shipping member may be received through an opening in the housing. The locking portion may be received through an opening formed in a pusher adapter of the pusher assembly. Receipt of the locking portion through the opening of the pusher adapter may secure the pusher adapter relative to the housing.

In embodiments, the locking portion of the shipping member extends parallel to the base portion. The locking portion of the shipping member may extend perpendicular to the leg portion. A proximal end of the housing is configured for operable engagement with a stapling device.

A shipping member including a base portion including a planar body, a leg portion extending proximally from the base portion, and a locking portion disposed near a free end of the leg portion and extending parallel to the base portion. The locking portion may include a latch member. The leg portion extends perpendicular to the base portion and may define an opening.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
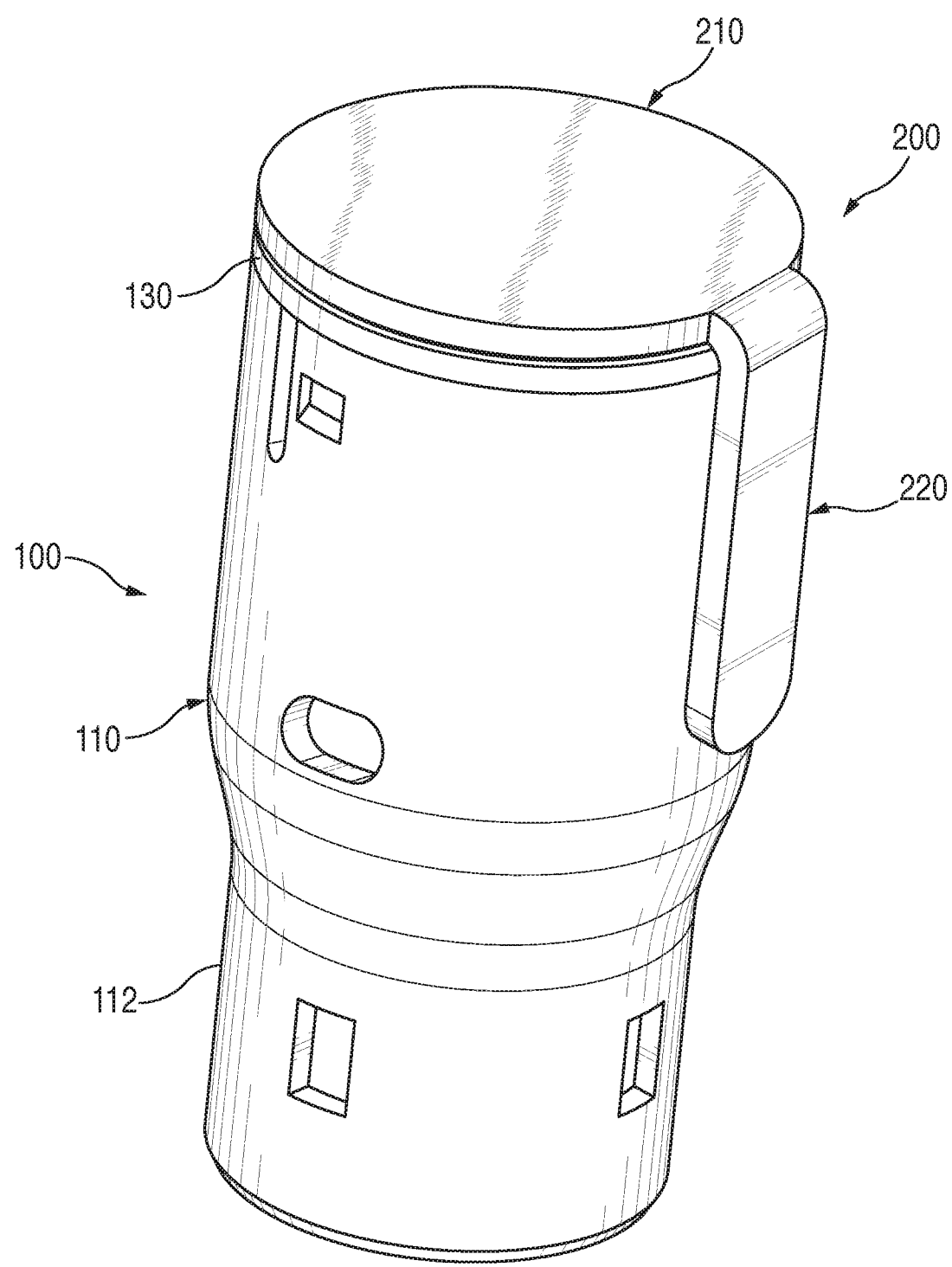
FIG. 1 is a perspective side view of a loading unit, according to an embodiment of the present disclosure, including a shipping member, according to an embodiment of the present disclosure, secured thereto.

Embodiments of the presently disclosed loading unit including a shipping member will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Figure 2:
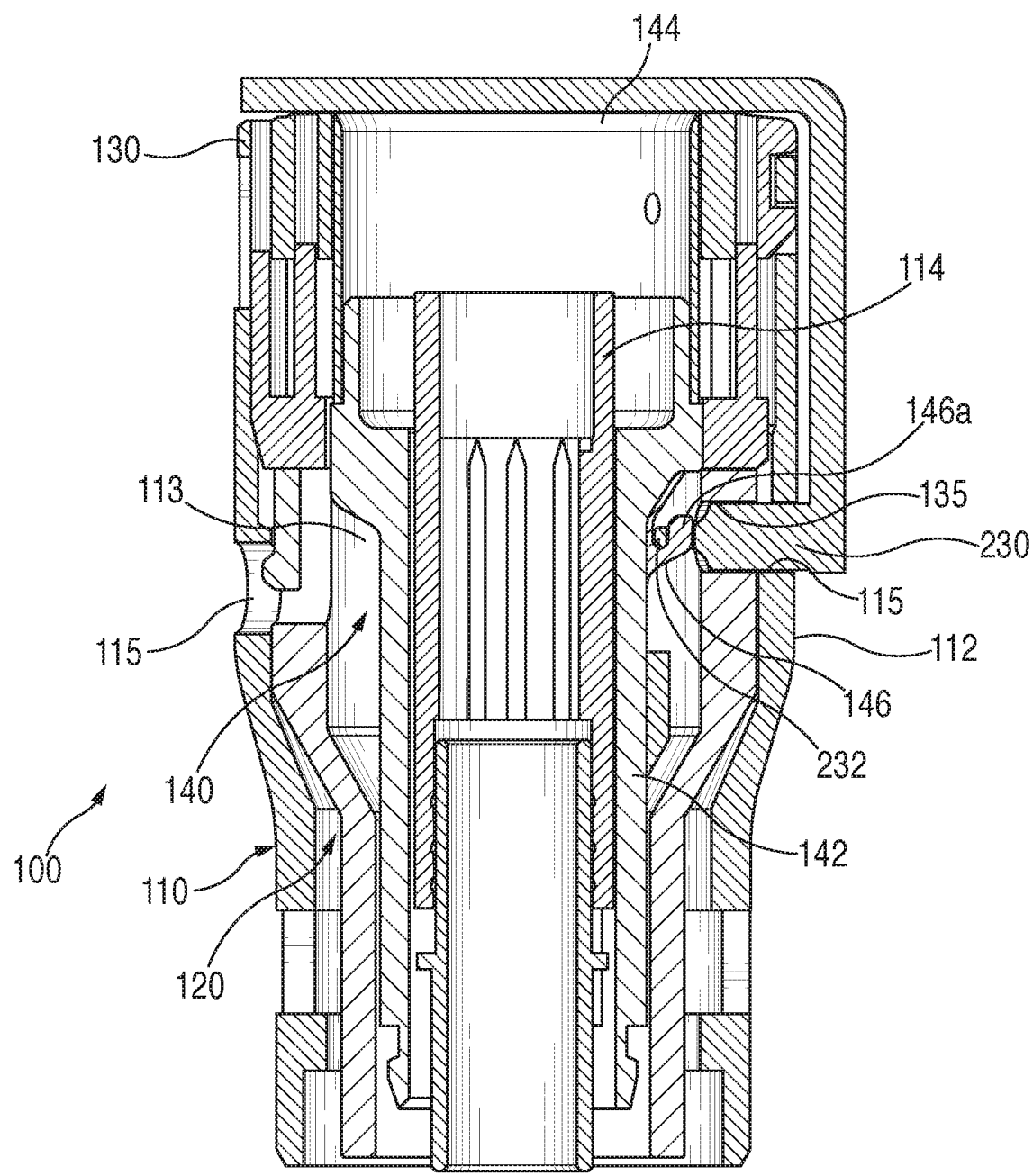
FIG. 2 is a cross-sectional side view of the loading unit and the shipping member shown in FIG. 1, including a knife carrier in a first or initial position.
Figure 3:
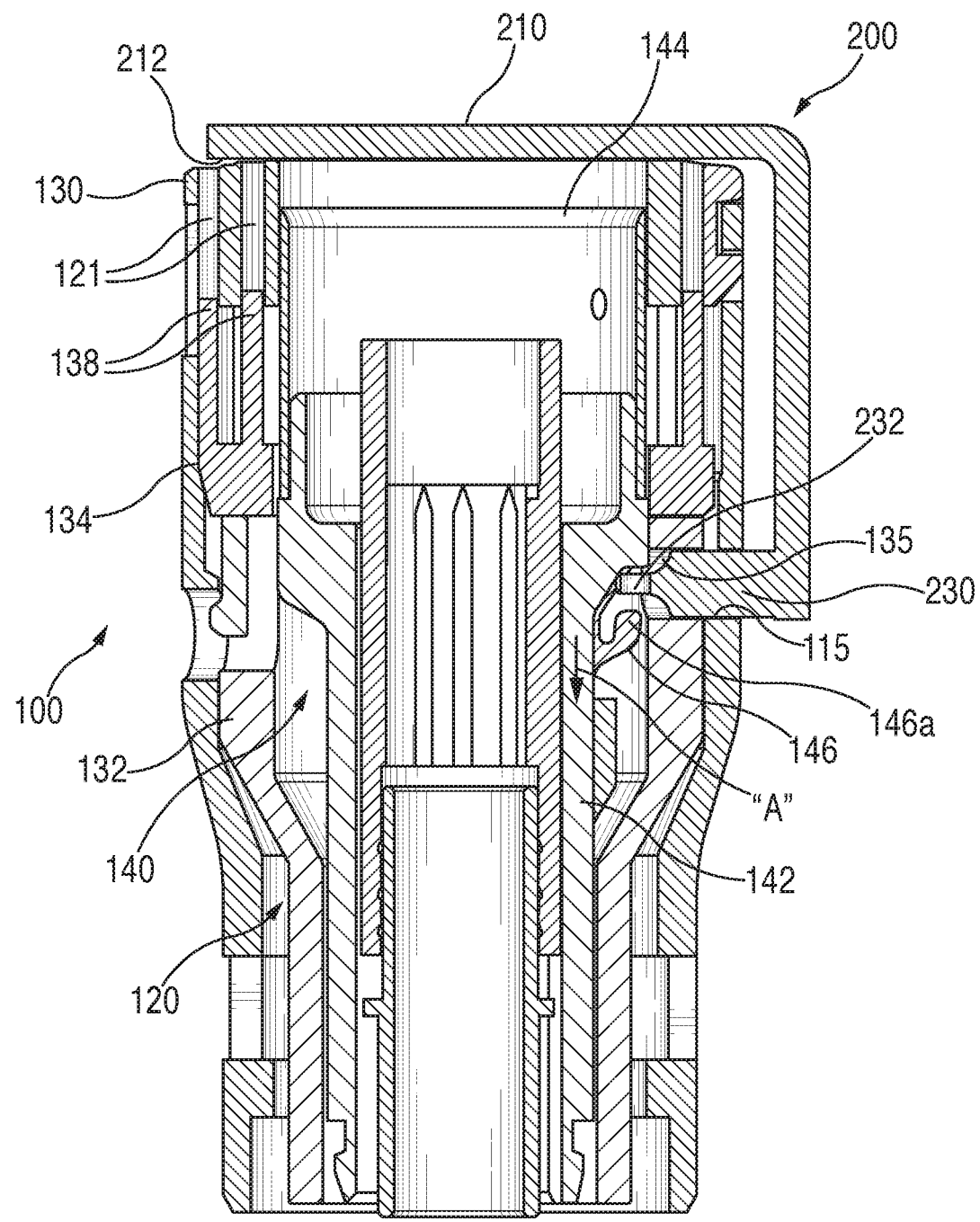
FIG. 3 is a cross-sectional side view of the loading unit and the shipping member shown in FIG. 2, including the knife carrier in a second or proximal position.
Figure 4:
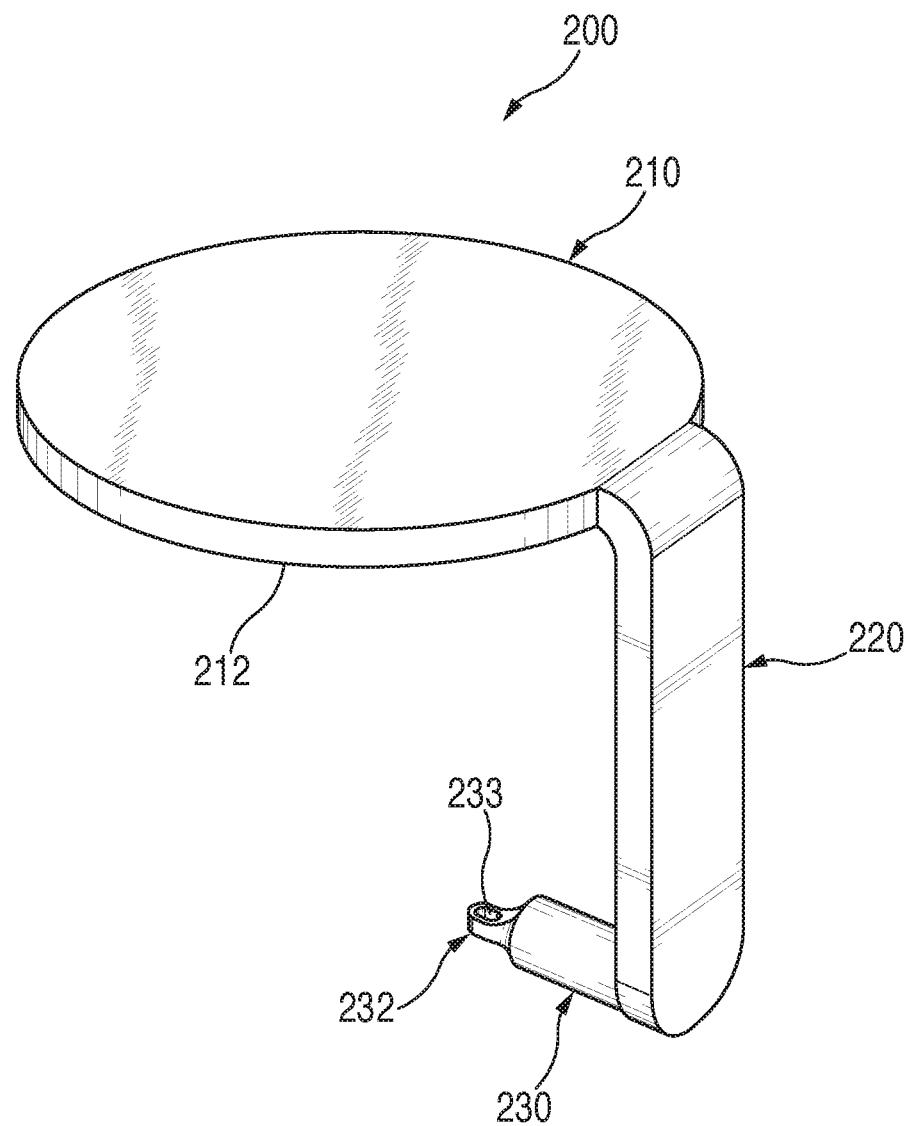
FIG. 4 is a perspective side view of the shipping member shown in FIG. 1.

With reference to FIGS. 1-3, a replaceable loading unit, according to an embodiment of the present disclosure, is shown generally as loading unit 100 and includes a shipping member, according to an embodiment of the present disclosure, shown generally as shipping cap 200. Loading unit 100 is configured for operable connection to a surgical stapling device (not shown). Shipping cap 200 is selectively received on a distal end of loading unit 100 and operates to maintain staples (not shown) within a staple cartridge 120 of loading unit 100. Shipping cap 200 also operates to prevent premature advancement of a staple pusher assembly 130 (FIG. 2) of loading unit 100 and a knife assembly 140 (FIG. 2) of loading unit 100 prior to and during attachment of loading unit 100 to an actuation unit (not shown) of the stapling device (not shown) or an adapter assembly (not shown) that is connected to the actuation unit (not shown) of the stapling device (not shown).

Although loading unit 100 will be described with reference to shipping cap 200, and shipping cap 200 will be described with reference to loading unit 100, it is envisioned that the aspects of the present disclosure may be modified for use with loading units and shipping caps having different configurations. Loading unit 100 will only be described to the extent necessary to fully disclose the aspects of the present disclosure. For a more detailed description of an exemplary loading unit, please refer to commonly owned U.S. Patent Application Publication No. 2013/0181035, the content of which is incorporated by reference herein in its entirety.

With continued reference to FIGS. 1-3, loading unit 100 includes a housing 110, a staple cartridge 120 selectively secured to a distal end of housing 110, a staple pusher assembly 130 operably received within housing 110, and a knife assembly 140 operably received within housing 110. Housing 110 of loading unit 100 includes an outer cylindrical portion 112 and an inner cylindrical portion 114. A plurality of ribs (not shown) interconnects outer and inner cylindrical portions 112, 114. Inner cylindrical portion 114 and outer cylindrical portion 112 of housing 110 are coaxial and define a recess 113 therebetween configured to operably receive staple pusher assembly 120 and knife assembly 140. A proximal end of housing 110 is configured for selective connection to an actuation unit (not shown) of a stapling device (not shown) or an adapter assembly (not shown) that is connected to an actuation unit (not shown) of a stapling device (not shown). As shown, housing 110 of loading unit 100 is configured for bayonet coupling to the actuation unit and/or the adapter assembly, however, it is envisioned that housing 110 may be connected to the actuation unit and/or the adapter assembly in any suitable manner.

With particular reference to FIGS. 2 and 3, outer cylindrical portion 112 of housing 110 defines an opening 115 longitudinally spaced from the distal end of loading unit 100 and extending through outer cylindrical portion 112. As will be discussed in further detail below, opening 115 in outer cylindrical portion 112 of housing 110 is configured to selectively receive a locking portion 230 of shipping cap 200.

Staple cartridge 120 of loading unit 100 is disposed on a distal end of housing 110 and includes a plurality of staple pockets 121 configured to selectively retain a plurality of staples (not show). Staple cartridge 120 may be selectively secured to housing 110 to allow replacement of staple cartridge 120 to permit reuse of the actuation unit with a fresh cartridge. Alternatively, staple cartridge 120 is securely affixed to housing 110 allowing for only a single use of loading unit 100.

With continued reference to FIGS. 2 and 3, staple pusher assembly 130 of loading unit 100 includes a pusher adapter 132 and a pusher 134. A proximal end of pusher adapter 132 is configured for operable connection to a drive mechanism (not shown) for advancing pusher adapter 132 and pusher 134 from a first or proximal position (FIG. 2) to a second or distal position (not shown) during actuation of the stapler device (not shown). Pusher adapter 132 of staple pusher assembly 130 defines an opening 135 positioned to align with opening 115 formed in outer cylindrical portion 112 of housing 110 when pusher adapter 132 is in the proximal position (FIG. 2). As shown, the diameters of opening 135 in pusher adapter 132 and opening 115 in outer cylindrical portion 112 of housing 110 are substantially equal in size and, as will be described in further detail below, are only slightly larger then the diameter of locking portion 230 of shipping cap 200. Pusher 134 includes a plurality of pusher members 138 (FIG. 2) aligned with staples (not shown) received within staple pockets 121 of staple cartridge 120. Advancement of pusher 134 relative to staple cartridge 120 causes ejection of the staples from staple cartridge 120.

Figure 6:
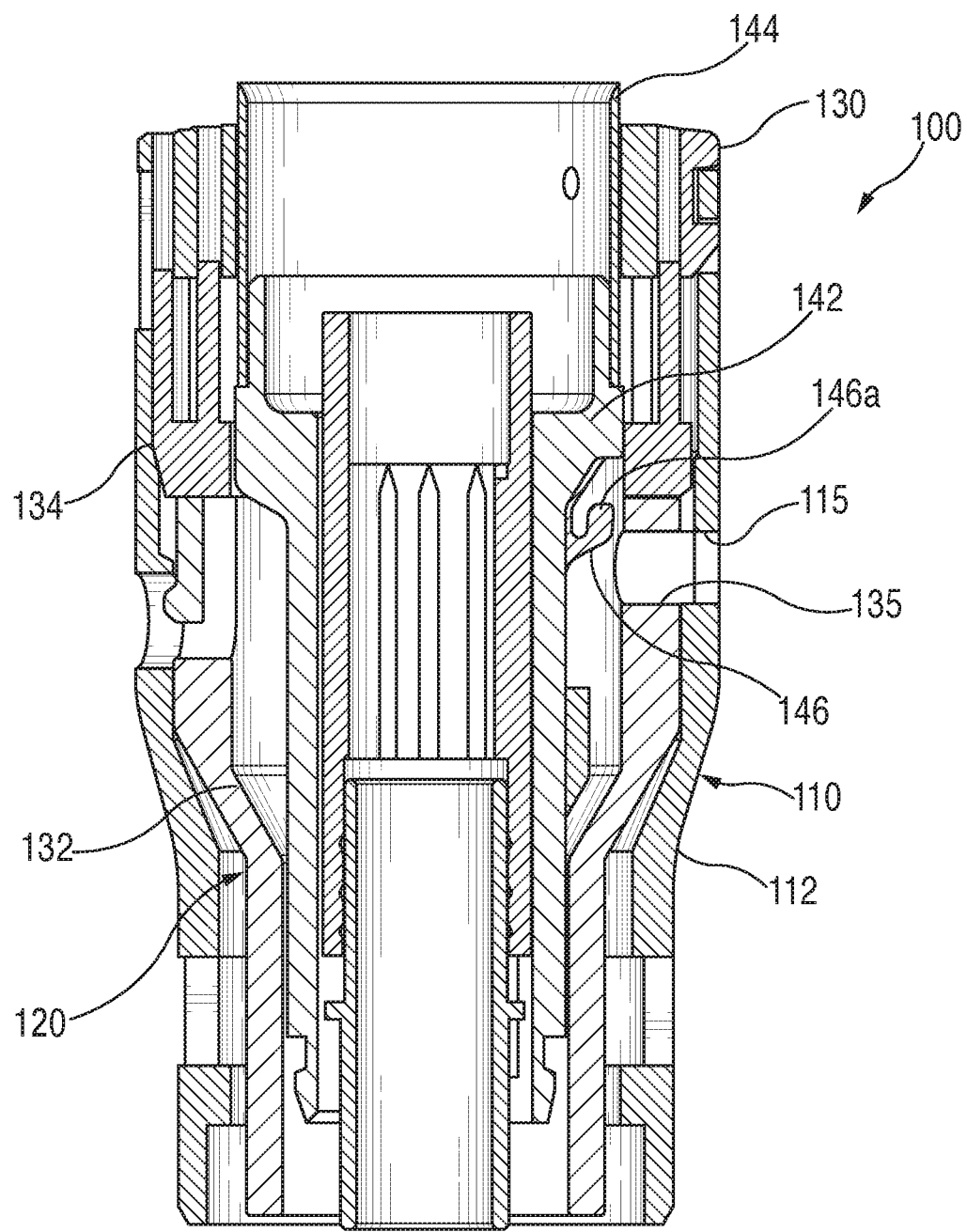
FIG. 6 is a cross-sectional side view of the loading unit shown in FIG. 5, including the knife carrier in a third or distal position.

Still referring to FIGS. 2 and 3, knife assembly 140 of loading unit 100 includes a knife carrier 142 and a circular knife 144. A proximal end of knife carrier 142 is configured for operable connection with a drive mechanism (not shown). As will be described in further detail below, the drive mechanism is configured to move knife carrier 142 and circular knife 144 from a first or initial position (FIG. 2) proximally to a second or retracted position (FIG. 3) to permit the separation of shipping cap 200 from loading unit 100, and subsequently to move knife carrier 142 and circular knife 144 distally to a third or advanced position (FIG. 6) to cause the cutting of tissue (not shown) disposed adjacent to staple cartridge 120 and within the staple line of staple cartridge 120.

Knife carrier 142 of knife assembly 140 includes a hook member 146 configured to selectively engage shipping cap 200. Although shown as being configured in the shape of a hook, it is envisioned that hook member 146 may be include any suitable shape for selectively engaging shipping cap 200. Hook member 146 opens in a distal facing direction and includes an engagement portion 146a extending longitudinally relative to knife carrier 142 and is configured to be received within an opening 233 formed in a latch member 232 of locking portion 230 of shipping cap 200 when knife carrier 142 is in the first position (FIG. 2). Engagement portion 146a may include an enlarged portion (not shown) or be otherwise configured to be snuggly received, i.e., friction fit, within opening 233 of latch member 232 of locking portion 230 to prevent inadvertent disengagement of hook member 146 from latch member 232 during shipping, installation, and/or placement of loading unit 100. As noted above, knife carrier 142 of knife assembly 140 is configured to be retracted proximally to the second or retracted position (FIG. 3) to disengage engagement portion 146a of hook member 146 from latch member 232 of locking portion 230 of shipping member 200. As will be described in further detail below, once latch member 232 of locking portion 230 is no longer engaged by hook member 146, shipping cap 200 may be separated from loading unit 100 thereby permitting advancement of knife carrier 142 to the third or advanced position (FIG. 6) to cause the cutting of tissue.

With reference now to FIGS. 1-4, shipping cap 200 is configured to be selectively received on a distal end of loading unit 100. Shipping cap 200 includes a base portion 210, a leg portion 220, and a locking portion 230. Although shown as being of one-piece construction, i.e., integrally or monolithically formed, it is envisioned that base portion 210, leg portion 220, and/or locking portion 230 may be independently formed and secured together with adhesive, welding, or in any other suitable manner.

As shown, base portion 210 of shipping cap 200 includes a substantially flat or planar body having a circular shape. Although shown having a circular shape, it is envisioned that base portion 210 may include any shape corresponding to the cross-sectional shape of loading unit 100 (FIG. 1). It is further envisioned that base portion 210 may be conical in shape or otherwise configured to facilitate insertion and positioning of loading unit 100 within tissue (not shown) of a patient (not shown).

A proximal facing surface 212 of base portion 210 of shipping cap 200 forms a staple retaining surface configured to abut staple cartridge 120 of loading unit 100 when shipping cap 100 is attached to the distal end of loading unit 100. Staple retaining surface 212 operates to retain staples (not shown) within staple pockets 121 of staple cartridge 120 during shipment and attachment of loading unit 100 to an actuation unit (not shown) of the stapling device (not shown) or an adapter (not shown) that is connected to the actuation unit of the stapling device. Although shown as being circular so as to correspond with the cross-sectional shape of staple cartridge 120 of loading unit 100, it is envisioned that staple retaining surface 212 of base portion 210 may be modified to correspond with staple cartridges having other cross-sectional configurations.

Leg portion 220 of shipping cap 200 extends proximally from base portion 210. As noted above, leg portion 220 may be integrally formed with base portion 210, or may be independently formed and fixedly secured to base portion 210. Leg portion 220 includes an elongated substantially rigid body and is configured to extend between staple cartridge 120 of loading unit 100 and opening 115 formed in outer cylindrical portion 112 of housing 110 of loading unit 100. Leg portion 220 may include a tab (not shown) or other feature configured for engagement by a user to facilitate separation of shipping cap 200 from loading unit 100.

Locking portion 230 of shipping cap 200 is disposed on a free end of leg portion 220 and extends radially inward from leg portion 220. Although shown as extending perpendicular to leg portion 220 of shipping cap 200 and extending parallel to base portion 210 of shipping cap 200, it is envisioned that locking portion 230 may be otherwise configured relative to base portion 210 and leg portion 220. For example, locking portion 230 may extend away from base portion 210 and at an angle relative to leg portion 220.

Although shown having a substantially cylindrical shape, it is envisioned that locking portion 230 of shipping cap 200 may include any other suitable shape. As discussed above, in some embodiments, the diameter of locking portion 230 is the same as or only slightly smaller then the diameter of opening 115 in outer cylindrical portion 112 of housing 110 of loading unit 100 and opening 135 in pusher adapter 132 of pushing assembly 130 of loading unit 100. The relative size of the diameters of opening 115 in outer cylindrical portion 112 of housing 110 and opening 135 in pusher adapter 132 of pushing assembly 130 and the diameter of locking portion 230 of shipping cap 200 ensures pusher adapter 132 of pushing assembly 130 is fixedly maintained within housing 100 when shipping cap 200 is attached to loading unit 100. The relative size of the diameters of openings 115, 135 and locking portion 230 also ensures that shipping cap 200 is fixedly maintained relative to loading unit 100, thereby maintaining base portion 210 of shipping cap 200 securely against staple cartridge 120 of loading unit 100. Locking portion 230 of shipping cap 200 is of sufficient length to be received through opening 115 formed in outer cylindrical portion 112 of housing 110 of loading unit 100 and through opening 135 formed in pusher adapter 132 of pusher assembly 130 of loading unit 100. As noted above, receipt of locking portion 230 of shipping cap 200 within opening 135 of pusher adapter 132 secures pusher adapter 132 relative to housing 110 and prevents premature advancement of pusher adapter 132.

Latch member 232 of locking portion 230 of shipping cap 200 is formed on a free end of locking portion 230 and defines an opening 233. As described above, opening 233 is configured to selectively receive engagement portion 146a of hook member 146 formed on knife carrier 142 of knife assembly 140 of loading unit 100.

When loading unit 100 is in a first or locked condition (FIG. 2), shipping cap 200 is securely received on the distal end of loading unit 100. In particular, locking portion 230 of shipping cap 200 is received within opening 115 formed in outer cylindrical portion 112 of housing 110 of loading unit 100 and through opening 135 formed in pusher adapter 132 of pusher assembly 130 of loading unit 100 such that staple retaining surface 212 of base portion 210 of shipping cap 200 is maintained adjacent staple cartridge 120 of loading unit 100. In this manner, staple retaining surface 212 of shipping cap 200 retains staples (not shown) within staple pockets 121 of staple cartridge 120 of loading unit 100. In the locked condition, knife carrier 142 of knife assembly 140 of loading unit 100 is in the first or initial position.

Shipping cap 200 is securely attached to loading unit 100 during the assembly of loading unit 100. More particularly, shipping cap 200 is secured to loading unit 100 subsequent to attachment of staple cartridge 120 to housing 110 of loading unit 100 to retain staples (not shown) within staple pockets 121 of staple cartridge 120. Prior to attachment of shipping cap 200 to loading unit 100, knife carrier 142 of knife assembly 140 is maintained in the second or retracted position (FIG. 3) to permit complete reception of locking portion 230 of shipping cap 200 through opening 115 in outer cylindrical portion 112 of housing 110 and through opening 135 in pusher adapter 132 of pusher assembly 130. Once locking portion 230 of shipping cap 200 is fully received within openings 115, 135, knife carrier 142 of knife assembly 144 is advanced to the initial position (FIG. 2) to cause engagement portion 146a of hook member 146 of knife carrier 140 to be received within opening 233 of latch member 232 of locking member 230 of shipping cap 200, thereby securing shipping cap 200 to loading unit 100.

Shipping cap 200 remains on loading unit 100 during shipping of loading unit 100 and during attachment of loading unit 100 to an actuation unit (not shown) of a stapling device (not shown) or an adapter assembly (not shown) that is connected to an actuation unit (not shown) of a stapling device (not shown). Once loading unit 100 is operably secured to the stapling device, retraction of knife carrier 142 of knife assembly 140 of loading unit 100 to the retracted position, as indicated by arrow "A" in FIG. 3, permits separation of shipping cap 200 from loading unit 100. In some embodiments, a chip (not shown) retained with loading unit 100 communicates with the actuation assembly of the stapling device to cause retraction of knife carrier 142. Alternatively, knife carrier 142 of knife assembly 140 is manually retracted by the user. As noted above, retraction of knife carrier 142 may occur any time subsequent to operable attachment of loading unit 100 to the stapling device. In some embodiments, shipping cap 200 remains attached to loading unit 100 subsequent to operable attachment of the loading unit 100 to the stapling device to facilitate placement of loading unit 100 within a patient. Alternatively, shipping cap 200 is immediately separable from loading unit 100 upon operable attachment of the loading unit 100 with the stapling device.

Figure 5:
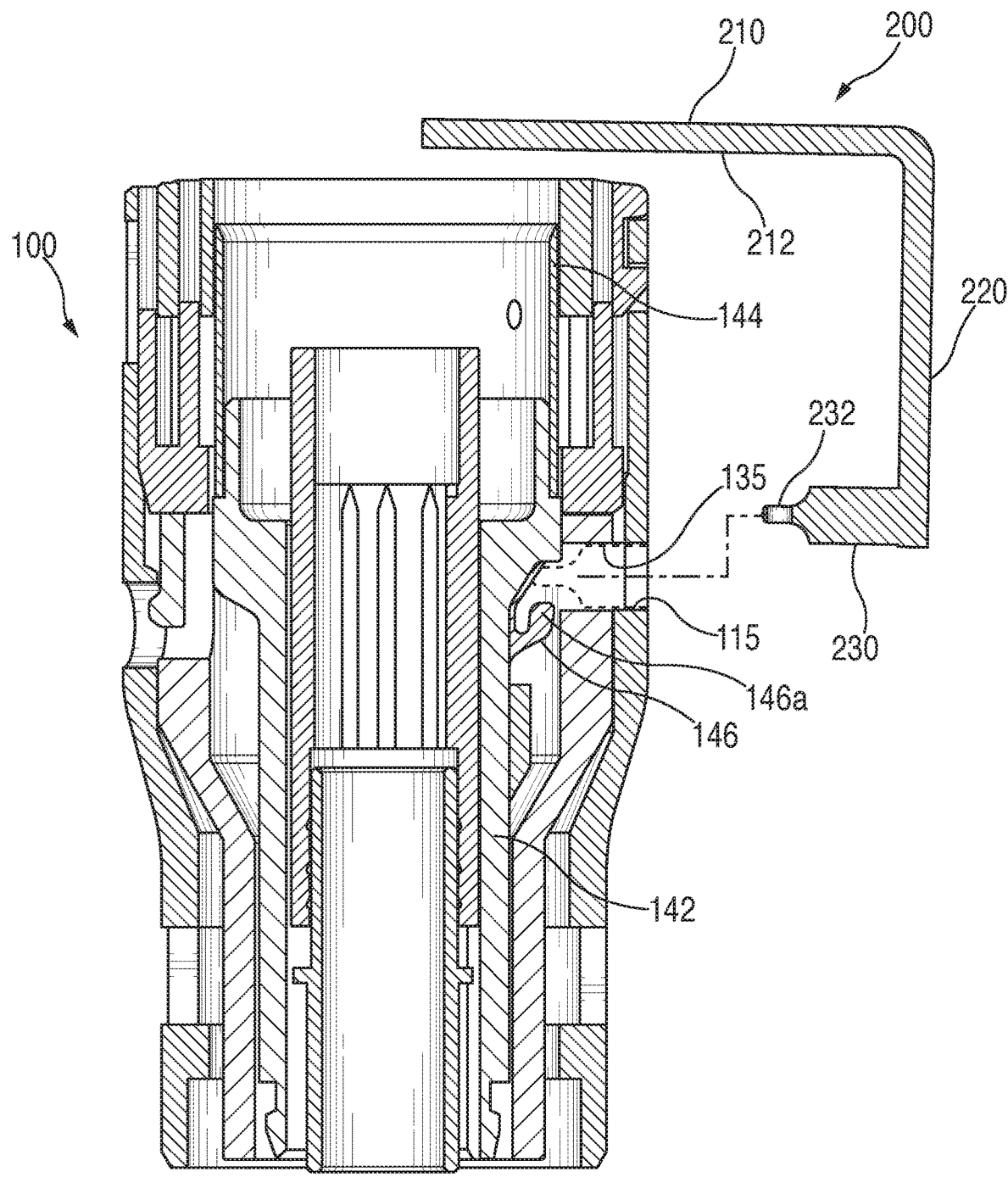
FIG. 5 is a cross-sectional side view of the loading unit and the shipping member shown in FIG. 3, separated from one another.

With reference now to FIG. 5, upon movement of knife carrier 142 of knife assembly 140 to the retracted position, shipping cap 200 may be separated from loading unit 100. In particular, locking portion 230 of shipping cap 200 is withdrawn from within opening 135 in pusher adapter 132 of pusher assembly 130 and from within opening 115 in outer cylindrical portion 112 of housing 110. Once shipping cap 200 is separated from loading unit 100, loading unit 100 may be used in a traditional manner.

In any of the embodiments described herein, the shipping cap can be used on a surgical stapling instrument that has a knife assembly permanently attached to the handle portion of the instrument, and can be used in conjunction with instruments having manually operated, manually powered handle portions, or motorized handle portions or other motorized components. In any of the embodiments described herein, the shipping cap can be used on a stapling component made for use in a robotic surgical system.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A shipping member for retaining staples within a loading unit of a circular stapler, the shipping member comprising:
    a base portion including a planar body configured to retain the staples within the loading unit, the planar body being circular;
    a leg portion extending proximally from and perpendicular to the circular planar body of the base portion; and
    a locking portion extending from a free end of the leg portion and extending parallel to the base portion, the locking portion including a latch member;
    wherein a proximal facing surface of the base portion forms a staple retaining surface.

2. The shipping member of claim 1, wherein the latch member of the locking portion defines an opening.

3. The shipping member of claim 2, wherein the opening includes a central axis, the central axis of the opening extending perpendicularly to the base portion.

4. The shipping member of claim 1, wherein the latch member of the locking portion is configured to engage a knife pusher assembly of the loading unit.

5. The shipping member of claim 1, wherein the planar body corresponds in shape to a cartridge assembly of the loading unit.

6. The shipping member of claim 1, wherein an engagement portion of a lock member extends perpendicularly to the locking portion.

7. The shipping member of claim 1, wherein the locking portion is configured to be received through an opening in a housing of the loading unit.

8. The shipping member of claim 1, wherein the base portion, the leg portion, and the locking portion are integrally formed.

9. The shipping member of claim 1, wherein the base portion, the leg portion, and the locking portion are monolithic.

10. The shipping member of claim 1, wherein the locking portion is longitudinally spaced from the base portion.

11. The shipping member of claim 1, wherein the latch member extends perpendicular to the leg portion.

12. The shipping member of claim 1, wherein the planar body defines a plane and the leg portion defines a longitudinal axis, the longitudinal axis being perpendicular to the plane.

13. The shipping member of claim 1, wherein the locking portion is cylindrical.

14. The shipping member of claim 1, wherein the locking portion is configured to prevent movement of a staple pusher of the loading unit.

15. The shipping member of claim 1, wherein the latch member is configured to prevent advancement of a knife pusher of the loading unit.

16. A shipping member for retaining staples within a loading unit of a circular stapler, the shipping member comprising:
    a base portion including a circular planar body configured to retain the staples within the loading unit;
    a leg portion extending proximally from and perpendicular to the circular planar body of the base portion; and
    a locking portion extending from a free end of the leg portion and extending parallel to the base portion, the locking portion being configured to prevent movement of a staple pusher of the loading unit and including a latch member configured to prevent advancement of a knife pusher of the loading unit.

17. A shipping member for retaining staples within a loading unit of a circular stapler, the shipping member comprising:
    a base portion including a planar body configured to retain the staples within the loading unit, the planar body being circular;
    a leg portion extending proximally from and perpendicular to the circular planar body of the base portion; and
    a locking portion extending from a free end of the leg portion and extending parallel to the base portion, the locking portion including a latch member;
    wherein the latch member of the locking portion is configured to engage a knife pusher assembly of the loading unit.

18. The shipping member of claim 17, wherein a proximal facing surface of the base portion forms a staple retaining surface.

19. The shipping member of claim 17, wherein the locking portion is configured to be received through an opening in a housing of the loading unit.

20. The shipping member of claim 17, wherein the locking portion is configured to prevent movement of a staple pusher of the loading unit.

* * * * *